US008592336B2

(12) United States Patent
Lee et al.

(10) Patent No.: US 8,592,336 B2
(45) Date of Patent: Nov. 26, 2013

(54) CATALYSTS FOR RING-CLOSING METATHESIS

(71) Applicant: Agency for Science, Technology and Research, Singapore (SG)

(72) Inventors: Su Seong Lee, Singapore (SG); Jaehong Lim, Singapore (SG); Siti Nurhanna Binte Riduan, Singapore (SG); Jackie Y. Ying, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/747,811

(22) Filed: Jan. 23, 2013

(65) Prior Publication Data

US 2013/0131353 A1    May 23, 2013

Related U.S. Application Data

(63) Continuation-in-part of application No. 12/296,903, filed as application No. PCT/SG2007/000096 on Apr. 11, 2007.

(60) Provisional application No. 60/790,808, filed on Apr. 11, 2006.

(51) Int. Cl.
 *B01J 31/10* (2006.01)

(52) U.S. Cl.
 USPC ............ 502/155; 502/100; 502/152; 502/439

(58) Field of Classification Search
 USPC ................... 502/155, 100, 152, 439
 See application file for complete search history.

(56) References Cited

U.S. PATENT DOCUMENTS

| 6,372,687 B1 | 4/2002 | Hagemeyer |
| 6,544,923 B1 | 4/2003 | Ying |
| 6,900,347 B2 | 5/2005 | Paulson et al. |
| 7,268,242 B2 | 9/2007 | Pederson et al. |

FOREIGN PATENT DOCUMENTS

| JP | H10-175882 A | 6/1998 |
| JP | H10-180114 A | 7/1998 |
| JP | H11-192432 A | 7/1999 |
| JP | 2002-154990 A | 5/2002 |
| JP | 2003-089689 A | 3/2003 |
| JP | 2004-500364 A | 1/2004 |
| JP | 2004-506646 A | 3/2004 |
| JP | 2005-515260 A | 5/2005 |
| JP | 2005-255428 A | 9/2005 |
| JP | 2005-255581 A | 9/2005 |
| WO | 01/52985 A2 | 7/2001 |

OTHER PUBLICATIONS

Akiyama, R. and Kobayashi, S., "A Novel Polymer-Supported Arene-Ruthenium Complex for Ring-Closing Olefin Metathesis", Angewandte Chemie International Edition in English, Jul. 15, 2002, pp. 2602-2604, vol. 41, Issue 14.
Audic, N. et al., "An Ionic Liquid-Supported Ruthenium Carbene Complex: A Robust and Recyclable Catalyst for Ring-Closing Olefin Metathesis in Ionic Liquids", Journal of the American Chemical Society, Aug. 6, 2003, pp. 9248-9249, vol. 125, Issue 31.
Barrett, A.G.M. et al., "ROMP-Spheres: A Novel High-Loading Polymer Support Using Cross Metathesis between Vinyl Polystyrene and Norbornene Derivative", Organic Letters, Oct. 7, 1999, pp. 1083-1086, vol. 1, Issue 7.
De Clercq, B. et al. Hetergonation of a Shiff Base Substituted Grubbs Catalyst and Ru-Dimer to perform romp reactions. Nato Science Series, II: Mathematics, Physics and Chemistry (2002), 56(Ring Opening Metathesis Polymerization and Related Chemistry, 451-464.
Elias, Xavier et al. "Hybrid organic-inorganic materials derived from a monosilylaed Hoveyda-type ligand as recyclable diene and enyne metathesis catalysts", Adv. Synth. Catal., vol. 348, 2006, 751-762.
Fischer, D. and Blechert, S., "Highly Active Silica Gel-Supported Metathesis (Pre)Catalysts", Advanced Synthesis & Catalysis, Aug. 2005, pp. 1329-1332, vol. 347, Issue 10.
Gessler, S. et al., "Synthesis and metathesis reactions of a phosphine-free dihydroimidazole carbine ruthenium complex", Tetrahedron Letters, Dec. 16, 2000, pp. 9973-9976, vol. 41, Issue 51.
Grela, K. et al., "A PS-DES immobilized ruthenium carbene: a robust and easily recyclable catalyst for olefin metathesis", Tetrahedron Letters, Dec. 9, 2002, pp. 9055-9059, vol. 43, Issue 50.
Halbach, T.S. et al., "Novel Ruthenium-Based Metathesis Catalysts Containing Electron-Withdrawing Ligands: Synthesis, Immobilization, and Reactivity", The Journal of Organic Chemistry, Jun. 10, 2005, pp. 4687-4694, vol. 70, Issue 12.
Han et al. "Generalized fluorocarbon-surfactant-mediated synthesis of nanoparticles with various mesoporous structures". Agnew. Chem. Int. Ed., vol. 44, Jan. 1, 2005, pp. 288-289.
Huang, X. and Ying, J.Y., "Asymmetric transfer hydrogenation over Ru-TsDPEN catalysts supported on siliceous mesocelluar foam", Chemical Communications, May 14, 2007, pp. 1825-1827, vol. 18.
Kingsbury, J.S. et al., "A Recyclable Ru-Based Metathesis Catalyst", Journal of the American Chemical Society, Feb. 3, 1999, pp. 791-799, vol. 121, Issue 4.
Kingsbury, J.S. et al., "Immobilization of Olefin Metathesis Catalysts on Monolithic Sol-Gel: Practical, Efficient, and Easily Recyclable Catalysts for Organic and Combinatorial Synthesis", Angewandte Chemie International Edition in English, Nov. 19, 2001, pp. 4251-4256, vol. 40, Issue 22.
Lettow, J.S. et al., "Hexagonal to Mesocellular Foam Phase Transition in Polymer-Templated Mesoporous Silicas", Langmuir, Oct. 31, 2000, pp. 8291-8295, vol. 16, Issue 22.
Lettow, J.S. et al., "Small-Angle Neutron Scattering and Theoretical Investigation of Poly(ethylene oxide)-Poly (propylene oxide)-Poly-(ethylene oxide) Stabilized Oil-in-Water Microemulsions", Langmuir, Jun. 21, 2005, vol. 21, Issue 13.
Matsugi, M. and Curran, D.P., "Synthesis, Reaction, and Recycle of Light Fluorous Grubbs-Hoveyda Catalysts for Alkene Metathesis", The Journal of Organic Chemistry, Mar. 4, 2005, pp. 1636-1642, vol. 70, Issue 5.

(Continued)

*Primary Examiner* — Melvin C Mayes
*Assistant Examiner* — Melissa Stalder
(74) *Attorney, Agent, or Firm* — Klarquist Sparkman, LLP

(57) ABSTRACT

A catalyst composition is provided, which may be used for ring closing metathesis. In the composition, a catalyst is immobilized on a siliceous mesocellular foam support. A suitable catalyst for use in the composition is a Grubbs-type catalyst or a Hoveyda-Grubbs-type catalyst.

9 Claims, No Drawings

(56) References Cited

OTHER PUBLICATIONS

Mayr, M. et al., "Monolithic Materials: New High-Performance Supports for Permanently Immobilized Metathesis Catalysts", Angewandte Chemie International Edition in English, Oct. 15, 2001, pp. 3839-3842, vol. 40, Issue 20.

Melis, K. et al., Journal of Molecular Catalysis A: Chemical., "ROMP and RCM catalysed by {R3P)2Cl2Ru=CHPh immobilized on a mesoporous support", Mar. 28, 2001, pp. 47-56, vol. 169, Issues 1-2.

Michrowska, A. et al., "Nitro-Substituted Hoveyda-Grubbs Ruthenium Carbenes: Enhancement of Catalyst Activity through Electronic Activation", Journal of the American Chemical Society, Aug. 4, 2004, pp. 9318-9325, vol. 126, Issue 30.

Nieczypor, P. et al., "Synthesis and application of a new polystyrene-supported ruthenium carbene catalyst for alkene metathesis", Tetrahedron Letters, Oct. 1, 2001, pp. 7103-7105, vol. 42, Issue 40.

Pugin, B. and Muller, M. "Enantioselective Metal Complex Catalysts Immobilized on Inorganic Supports Via Carbamate Links", Heterogeneous Catalysis and Fine Chemicals III, 107-114 (Ed. Guisnet et al. 2003).

Schmidt-Winkel, P. et al., "Mesocellular Siliceous Foams with Uniformly Sized Cells and Windows", Journal of the American Chemical Society, Jan. 13, 1999, pp. 254-255, vol. 121, Issue 1.

Schmidt-Winkel, P. et al., "Microemulsion Templating of Siliceous Mesostructured Cellular Foams with Well-Defined Ultralarge Mesopores", Chemistry of Materials, Mar. 2000, pp. 686-696, vol. 12, Issue 3.

Schwab, P. et al., "A Series of Well-Defined Metathesis Catalysts-Synthesis of [RuCl2{====CHR')(PR3)2] and Its Reactions", Angewandte Chemie International Edition in English, Oct. 2, 1995, pp. 2039-2041, vol. 34, Issue 18.

Seiders, T.J. et al., "Enantioselective Ruthenium-Catalyzed Ring-Closing Metathesis", Organic Letters, Oct. 4, 2001, pp. 3225-3228, vol. 3, Issue 20.

Sinner, F. and Buchmeiser, M.R., "A New Class of Continuous Polymer Supports Prepared by Ring-Opening Metathesis Polymerization: A Straightforward Route to Functionalized Monoliths", Macromolecules, Aug. 8, 2000, pp. 5777-5786, vol. 33, Issue 16.

Verport, F. et al. "Romp and RCM catalysed by (R3P)2C12Ru=CHPh immobilized on a mesoporous support." Journal of Molecular Catalysis A: Chemical, vol. 169, 2001, pp. 47-58.

Yao, Q., "A Soluble Polymer-Bound Ruthenium Carbene Complex: A Robust and Reusable Catalyst for Ring-Closing Olefin Metathesis", Angewandte Chemie International Edition in English, Nov. 3, 2000, pp. 3896-3898, vol. 39, Issue 21.

Yao, Q. and Motta, A.R., "Immobilization of the Grubbs second-generation ruthenium-carbene complex on poly (ethylene glycol): a highly reactive and recyclable catalyst for ring-closing and cross-metathesis", Tetrahedron Letters., Mar. 8, 2004, pp. 2447-2451, vol. 45, Issue 11.

Yao, Q. and Zhang, Y., "Olefin Metathesis in the Ionic Liquid 1-Butyl-3-methylimidazolium Hexafluorophosphate Using a Recyclable Ru Catalyst: Remarkable Effect of a Designer Ionic Tag", Angewandte Chemie International Edition in English, Jul. 28, 2003, pp. 3395-3398, vol. 42, Issue 29.

Yao, Q. and Zhang, Y., "Poly(fluoroalkyl acrylate)-Bound Ruthenium Carbene Complex: A Fluorous and Recyclable Catalyst for Ring-Closing Olefin Metathesis", Journal of the American Chemical Society, Jan. 14, 2004, pp. 74-75, vol. 126, Issue 1.

Yo, H. and Ying, J.Y., "Generalized Fluorocarbon-Surfactant-Mediated Synthesis of Nanoparticles with Various Mesoporous Structures", Angewandte Chemie International Edition in English, Dec. 27, 2005, pp. 288-292, vol. 44, Issue 2.

Extended European Search Report issued in corresponding EP Patent Application No. 07748641.3-2103/2010318 dated Aug. 5, 2009.

2nd Examination Report dated Oct. 16, 2012 (issued in European Patent Application No. 07748641.3).

Office Action (Notice of Reasons for Rejection), dated Jul. 17, 2013, issued in corresponding JP Application No. 2009-505333.

CATALYSTS FOR RING-CLOSING METATHESIS

CROSS-REFERENCE TO RELATED APPLICATION

This application is a continuation-in-part of U.S. application Ser. No. 12/296,903, filed Dec. 10, 2008, which was the National Stage of International Application No. PCT/SG2007/000096, filed Apr. 11, 2007, which claims the benefit of U.S. Provisional Application No. 60/790,808, filed Apr. 11, 2006, the entire contents of each of which are hereby incorporated herein by reference.

FIELD OF INVENTION

This invention relates to a catalyst composition comprising a catalyst and a support, which may be used in a ring-closing metathesis (RCM) reaction.

BACKGROUND

Ring-closing metathesis (RCM) is used for synthesizing cyclic compounds.

RCM has played a key role in the generation of cyclic motifs since Grubbs and co-workers reported the now well-defined ruthenium catalysts. (See, for example, Schwab, P.; France, M. B.; Ziller, J. W.; Grubbs, R. H. *Angew. Chem. Int. Ed. Engl.* 1995, 34, 2039.) Grubbs catalysts and Hoveyda-Grubbs catalysts have found wide application, including in the synthesis of various heterocyclic and macrocyclic natural products, and other polymers. However, industry, including the pharmaceutical industry has not yet widely adopted RCM in large-scale manufacturing. Reasons for this include the high cost of the ruthenium-containing compounds, and the relatively high metal leaching.

Attempts have been made to immobilize these homogeneous catalytic complexes on several types of supports. Many groups have reported on the immobilization of the first- and second-generation Grubbs' catalysts (see, for example, Seiders, T. J.; Ward, D. W.; Grubbs, R. H. *Org. Lett.* 2001, 3, 3225). Others have reported on the immobilization of reusable modifications of these catalysts (see, for example, Kingsbury, J. S.; Harrity, J. P. A.; Bonitatebus, P. J.; Hoveyda, A. H. *J. Am. Chem. Soc.* 1999, 121, 791; and Gessler, S.; Randl, S.; Blechert, S. *Tetrahedron Lett.* 2000, 41, 9973). Immobilization techniques have been reported using: soluble polymers (see, for example, Yao, Q. *Angew. Chem. Int. Ed. Engl.* 2000, 39, 3896; and Yao, Q.; Motta, A. R. *Tetrahedron Lett.* 2004, 45, 2447); insoluble polymers (see, for example, Barrett, A. G. M.; Camp, S. M.; Roberts, R. S. *Org. Lett.* 1999, 1, 1083; Nieczypor, P.; Buchowicz, W.; Meester, W. J. N.; Rutjes, F. P. J. T.; Mol, J. C. *Tetrahedron Lett.* 2001, 42, 7103; Akiyama, R.; Kobayashi, S. *Angew. Chem. Int. Ed. Engl.* 2002, 41, 2602; Grela, K.; Tryznowski, M.; Bieniek, M. *Tetrahedron Lett.* 2002, 43, 9055; and Halbach, T. S.; Mix, S.; Fischer, D.; Maechling, S.; Krause, J. O.; Sievers, C.; Blechert, S.; Nuyken, O.; Buchmeiser, M. R. *J. Org. Chem.* 2005, 70, 4687); monolithic gels (see, for example, Kingsbury, J. S.; Garber, S. B.; Giftos, J. M.; Gray, B. L.; Okamoto, M. M.; Farrer, R. A.; Fourkas, J. T.; Hoveyda, A. H. *Angew. Chem. Int. Ed. Engl.* 2001, 40, 4251); ionic liquids (see, for example, Audic N.; Clavier, H.; Mauduit, M.; Guillemin, J.-C. *J. Am. Chem. Soc.* 2003, 125, 9248; and Yao, Q.; Zhang, Y. *Angew. Chem. Int. Ed. Engl.* 2003, 42, 3395); fluorous materials (see, for example, Yao, Q.; Zhang, Y. *J. Am. Chem. Soc.* 2004, 126, 74; and Matsugi, M.; Curran, D. P. *J. Org. Chem.* 2005, 70, 1636); and silica (see, for example, (Melis, K.; Vos, D. D.; Jacobs, P.; Verpoort, F. *J. Mol. Catal. A: Chem.* 2001, 169, 47). However, immobilized catalysts obtained by these methods generally also suffer from shortcomings, such as, low reactivity (e.g., due to diffusion-related issues), reduced activity upon reuse, requirement for further purification, etc.

Ring-opening metathesis polymerization (ROMP) by (a) glass-type (see, for example, Kingsbury, J. S.; Garber, S. B.; Giftos, J. M.; Gray, B. L.; Okamoto, M. M.; Farrer, R. A.; Fourkas, J. T.; Hoveyda, A. H. *Angew. Chem. Int. Ed. Engl.* 2001, 40, 4251) and (b) one-pot functionalized monolith (see, for example, Sinner, F.; Buchmeiser, M. R. *Macromolecules* 2000, 33, 5777; and Mayr, M.; Mayr, B.; Buchmeiser, M. R. *Angew. Chem. Int. Ed. Engl.* 2001, 40, 3839) have also been reported. Both seem to be complicated procedures, despite the apparent advantages of application to library generation and ability to be recycled.

A silica gel-supported metathesis catalyst has also been reported, with reported mild reaction conditions, high turnover number and ease of purification. (See Fischer, D.; Blechert, S. *Adv. Synth. Catal.* 2005, 347, 1329.) However, this catalyst does not recycle well, even for reaction involving a simple substrate. Only 68% yield was reported achieved in three runs.

Others have reported on the use of mesoporous compositions as supports for catalysts. (See, for example, U.S. Pat. No. 6,544,923 and Xiaohua Huang, Chem. Comm., 2007, DOI:10.1039/b615564).

Siliceous mesocellular foams (MCF) have been prepared having a three-dimensional, interconnected pore structure with ultralarge cell-like pores (e.g., 24-42 nm) that are connected by windows of, for example, 9-22 nm. (See, for example, Schmidt-Winkel, P.; Lukens, W. W., Jr.; Zhao, D.; Yang, P.; Chmelka, B. F.; Stucky, G. D. *J. Am. Chem. Soc.* 1999, 121, 254; Schmidt-Winkel, P.; Lukens, W. W., Jr., Yang, P.; Margolese, D. I.; Lettow, J. S.; Ying, J. Y.; Stucky, G. D. *Chem. Mater.* 2000, 12, 686; Lettow, J. S.; Han, Y. J.; Schmidt-Winkel, P.; Yang, P.; Zhao, D.; Stucky, G. D.; Ying, J. Y. *Langmuir* 2000, 16, 8291; Lettow, J. S.; Lancaster, T. M.; Glinka, C. J.; Ying, J. Y. *Langmuir* 2005, 21, 5738; and Yu, H.; Ying, J. Y. *Angew. Chem. Int. Ed.* 2005, 44, 288.)

In general, known procedures have not generated sufficiently efficient heterogenized catalysts for industrial applications. These immobilized catalysts have generally been difficult to prepare with high cost, poor environmental compatibility, and relatively poor catalytic activity.

SUMMARY

According to one broad aspect of the present invention, there is provided a catalyst composition comprising a ruthenium catalyst immobilized on a siliceous mesocellular foam support. In one embodiment, the ruthenium catalyst is a Grubbs catalyst or a Hoveyda-Grubbs catalyst.

According to another aspect of the present invention, there is provided a catalyst composition comprising a catalyst:

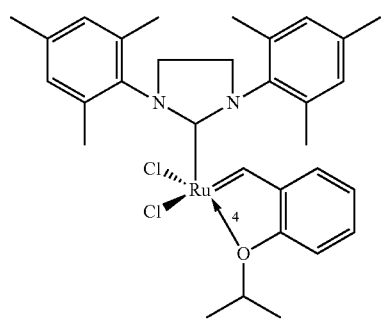

immobilized on a siliceous mesocellular foam support. The catalyst composition may be immobilized on the siliceous mesocellular foam support using a linking group comprising a carbamate or silyl group, for example. The carbamate may be any carbamate, including for example, —OC(O)NH—, or an alkylated carbamate such as —(CH$_2$)$_n$—OC(O)NH—, (n being for example 1, 2, 3, 4, 5, 6, 7, 8, 9, 10, 11 or 12). In exemplary embodiments, the carbamate or silyl group is attached to the siliceous mesocellular foam support through an alkyl spacer, such as, for example, a C$_1$-C$_6$ alkyl group. In further exemplary embodiments, the carbamate is an alkyl carbamate, including a C$_{1-12}$ carbamate, including for example a hexyl carbamate, pentyl carbamate, butyl carbamate, propyl carbamate, ethyl carbamate, or methyl carbamate, and the silyl group is substituted by one or two alkyl groups, including for example methyl groups. In a still further exemplary embodiments, the linking group is —X—C(O)N(H)CH$_2$CH$_2$CH$_2$—, wherein X is (CH$_2$)$_n$O or O, wherein n is 1, 2, 3, 4, 5, 6, 7, 8, 9, 10, 11 or 12, or the linking group is —Si(CH$_3$)$_2$—[(C$_1$-C$_6$)alkyl]$_n$—, wherein n is 0, 1, 2, 3, 4, 5, or 6. In a yet further exemplary embodiment, the linking group is attached to the 2-position of the catalyst:

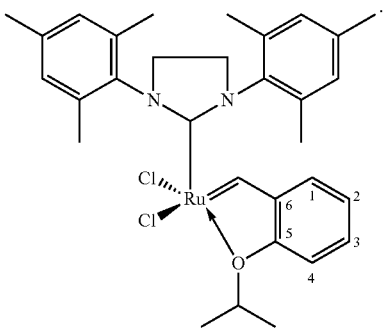

In another exemplary embodiment of the present invention, the siliceous mesocellular foam support comprises trimethylsilyl. In a further embodiment, the siliceous mesocellular foam support comprises spherical, monodisperse siliceous mesocellular foam microparticles. The siliceous mesocellular foam support may have an average pore diameter of about 24 to about 42 nm.

The catalyst composition according to the present invention may be used in a ring-closing metathesis reaction. In another invention embodiment, the catalyst composition is recycled for use in a further ring-closing metathesis reaction.

In a further broad aspect, the present invention provides a method for preparing a catalyst composition comprising immobilizing a Grubbs catalyst or a Hoveyda-Grubbs catalyst on a siliceous mesocellular foam support. In an exemplary embodiment, the catalyst is:

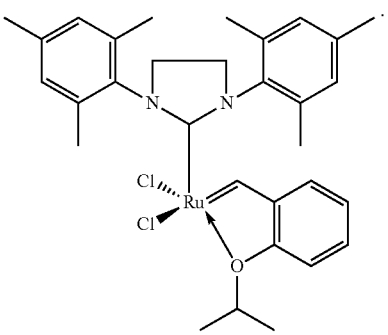

DETAILED DESCRIPTION

In the catalyst compositions of the invention, a catalyst is immobilized on a solid support comprising siliceous mesocellular foams (MCF). In one exemplary embodiment, spherical, monodisperse MCF is used as support for RCM catalysts including in, for example, batch reactor and packed bed reactor applications. In one embodiment, the pores have an average diameter of about 24 to about 42 nm, and may have open "windows" between the pores of about 9 to about 22 nm. Spherical MCF microparticles can be modified easily in terms of microstructure, pore size and surface chemistry for specific applications, as will be apparent to a person skilled in the art. The physical and chemical properties of MCF allow this material to be easily handled both at the laboratory and manufacturing scales.

The heterogenized catalysts of the present invention may be used for ring-closing metathesis (RCM). The catalyst compositions obtained according to the present invention may be beneficial to the chemical and pharmaceutical industries, such as, for example, in the large-scale production of drug candidates and food products, and the large-scale synthesis of fine and specialty chemicals. The catalyst compositions of the invention may be used on a wide variety of substrates under mild reaction conditions, including for ring closure of diene containing starting materials.

The catalyst immobilized on the MCF is not particularly limited. For RCM reactions, a ruthenium containing catalyst, such as a Grubbs type catalyst or a Hoveyda-Grubbs type catalyst, may be used. Hoveyda-Grubbs catalysts have the following general structure:

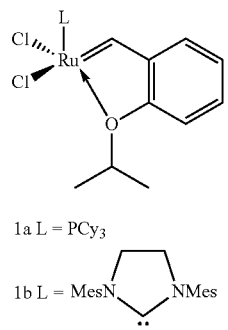

1a L = PCy$_3$

1b L = MesN⌒NMes wherein: P is platinum, Cy is cyclohexyl; and Mes is mesityl. Suitable derivatives of these catalysts are also within the contemplation of the present invention.

Ruthenium ligands may be immobilized on the support using a suitable linking group, including, without limitation, a Hoveyda-type ligand.

Non-limiting examples of other catalysts and linking groups are described in more detail herein.

The catalyst compositions of the invention were observed to exhibit activity and reusability suitable for RCM of various types of substrates.

In one exemplary embodiment of the present invention, immobilized second-generation Hoveyda-Grubbs catalysts using MCF as a solid support were obtained. Isopropoxystyrene ligands were fixed on the solid surface of the MCF support. The immobilization of catalysts 4a and 4b is illustrated in Scheme 1.

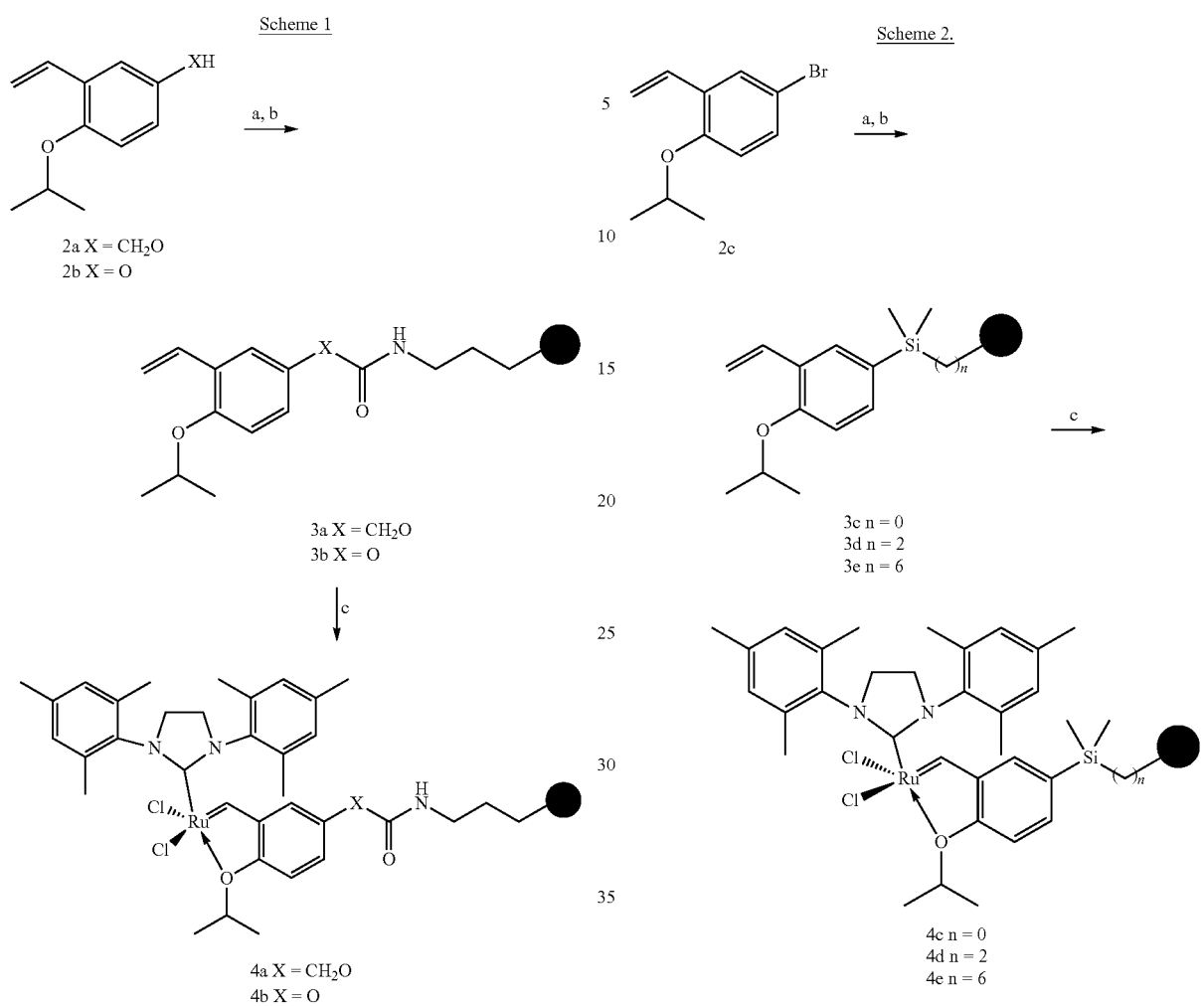

Reaction Conditions Scheme 1:

(a) 1.05 equiv. 3-isocyanopropyltriethoxysilane, 0.01 equiv. 4-dimethylaminopyridine, 3 equiv. triethylamine, dichloromethane (DCM), 45° C., 93-95%.

(b) Partially trimethylsilyl (TMS)-capped MCF, toluene, 100° C.; hexamethyldisilazane (HMDS), 80° C., 95-99%.

(c) 1.05 equiv. second-generation Grubbs' catalyst, 1.05 equiv. CuCl, DCM, 50° C., 90-94%.

In Scheme 1, starting with commercially available 3-bromo-4-hydroxybenzaldehyde and 2,5-dihydroxybenzaldehyde, the alcohol 2a and phenol 2b were readily prepared using known procedures. Intermediates 2a and 2b were immediately reacted with 3-isocyanylpropyltriethoxysilane to generate the corresponding carbamates, which were immobilized onto the surface of the partially trimethylsilyl-capped (TMS-capped) MCF by heating at 100° C. in toluene. In order to minimize the interference from MCF's residual surface silanols, the catalyst was post-capped by treatment with hexamethyldisilazane (HMDS) to obtain the isopropoxystyrene ligands 3a and 3b.

In another invention embodiment, heteroatom-free alkyl chains of tunable length were introduced to suppress the possibility of undesirable interference with the linker group in the catalytic reactions (Scheme 2).

Reaction Conditions Scheme 2:

(a) (i) 1.05 equiv. Mg, 0.01 equiv. $I_2$, tetrahydrofuran (THF), reflux, (ii) 3 equiv. $Me_2SiCl_2$ for 3c. $ClSiMe_2(CH)_2Cl$ for 3d, $ClSiMe_2(CH)_6Cl$ for 3e, 90-96%.

(b) Partially TMS-capped MCF, 3 equiv. triethylamine, toluene, room temperature; HMDS, 80° C., 99%.

(c) 1.05 equiv. second-generation Grubbs' catalyst, 1.05 equiv. CuCl, DCM, 50° C., 90-94%.

The 2-isopropoxy-4-bromostyrene 2c was readily silylated via Grignard reaction using three types of dichlorides, which were immobilized onto the surface of MCF by heating in toluene in the presence of triethylamine to derive the immobilized ligands 3c-3e in excellent yields.

The immobilized catalyst 4a-4e of Schemes 1 and 2 were isolated by refluxing the catalyst and the functionalized MCF 3a-3e in refluxing dichloromethane (DCM) in the presence of copper(I) chloride, followed by filtration and drying. Catalysts 4a-4e were prepared with different ligand and metal loadings, and stored for more than several months without losing any activity.

The immobilized catalysts 4a-4e were tested for RCM in dichloromethane (DCM), toluene or tetrahydrofuran (THF) by using diethyl diallylmalonate 5a and monitoring its conversion to the cyclized product 5b.

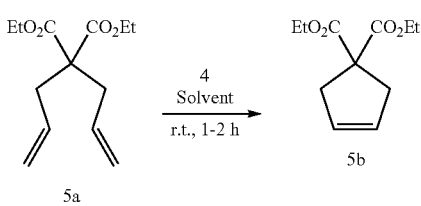 [SMILES: C=CCC(CC=C)(C(=O)OCC)C(=O)OCC ; CCOC(=O)C1(C(=O)OCC)CC=CC1]

RCM was determined as a percent (%) conversion (Conv) of diene 5a to product 5b over a time (t). The results are shown in Table 1. Unless otherwise noted, all reactions were performed over 5 mol % of catalyst (Cat) at 0.05 M in solvent at room temperature. The TMS/Ligand/Ru Loadings in mmol/g were determined by elemental analysis. The percent conversion was determined by gas chromatography (GC).

TABLE 1

| | | | Conversion (%) | | | |
|---|---|---|---|---|---|---|
| Cat | TMS/Ligand/Ru Loadings (mmol/g) | Solvent | t = 0.5 hour | t = 1 hour | t = 1.5 hours | t = 2 hours |
| 1 4a | 0.6/0.36/0.14 | DCM | | 99 | | 100 |
| | | Toluene | 90 | 98 | | |
| | | THF | 21 | | 63 | |
| 2 4a | 0.6/0.29/0.08 | DCM | 64 | 91 | 98 | 100 |
| | | Toluene | 88 | 97 | 100 | |
| | | THF | 9 | 27 | 56 | 78 |
| 3 4a | 0.6/0.36/0.26 | DCM | 60 | 91 | 100 | |
| | | Toluene | 63 | 72 | 76 | 78 |
| 4 4a | 0.6/0.36/0.26 | DCM[a] | 89 | 100 | | |
| | | Toluene[a] | 94 | 97 | | |
| 5 4a | 0.6/0.36/0.26 | DCM[b] | 31 | 58 | 75 | 86 |
| | | Toluene[b] | 43 | 51 | 55 | 59 |
| | | THF[b] | 2 | 6 | 19 | 18 |
| 6 4a | 0.8/0.22/0.18 | DCM[a] | 89 | 100 | | |
| | | Toluene[a] | 96 | 100 | | |
| 7 4a | 0/1.10/0.18 | DCM | 26 | 44 | 56 | 63 |
| 8 4a | 0/1.10/0.18 | DCM[a] | 58 | 85 | | 99 |
| 9 4b | 0/0.72/0.22 | DCM | 13 | 24 | 33 | 40 |
| | | Toluene | 26 | 37 | 43 | 48 |
| | | THF | 16 | 33 | 47 | 58 |
| 10 4b | 0.4/0.44/0.16 | DCM | 81 | 97 | 100 | |
| 11 4b | 0.4/0.44/0.16 | DCM[a] | 89 | 100 | | |
| | | Toluene[a] | 94 | 97 | | |
| 12 4c | 0.8/0.35/0.21 | DCM | 16 | 23 | 27 | 30 |
| 13 4d | 0.8/0.27/0.25 | DCM | 39 | 69 | 87 | 96 |
| 14 4e | 0.8/0.28/0.24 | DCM | 48 | 78 | 92 | 97 |
| 15 7 | — | DCM | 95 | 100 | | |
| | | Toluene | 85 | 94 | 97 | 99 |
| 16 1b | — | DCM | 98 | 100 | | |
| | | Toluene | 99 | 100 | | |
| | | THF | 87 | 98 | 99 | 100 |

[a]Performed at 0.1M in solvent.
[b]Performed over 2.5 mol % of catalyst.

It was observed that the reaction rate was dependent on the solvent used. It was observed that DCM and toluene were more effective than THF for all catalyst systems tested. The loadings of ligand and ruthenium did not seem to considerably affect the catalytic activity. However, it is noteworthy that the catalysts with very high ligand loadings and partially (<30%) loaded ruthenium showed reduced reaction rates (Entries 7-9). Without being bound by any theory, the high abundance of free ligands might have provided the reactive ruthenium carbene species more opportunities to return to the solid phase, which in turn slowed down the reaction. It was observed that the reaction became faster at a higher concentration (0.1 M) (Entries 4, 6, 8, and 11), without forming any significant amount of side-products as detected by nuclear magnetic resonance (NMR) spectroscopy. When a lower amount of 4a (2.5 mol %) was used, the reaction rate was decreased significantly (Entry 5).

It was observed that the reaction was accelerated with the increased flexibility of the linker group composed of non-coordinating hydrocarbon alkyl chain (Entries 12-14). Without being bound by any theory, when a short or rigid linker is used, the increased interaction between the catalytic center and the MCF surface may be interfering with and retarding the release and return of the ruthenium during the reaction.

To examine the role of the carbamate group in the linker, homogeneous catalyst 7 was prepared in good yield from alcohol 2a and n-butyl isocyanate in the same manner as 4a via intermediate 6 (Scheme 3).

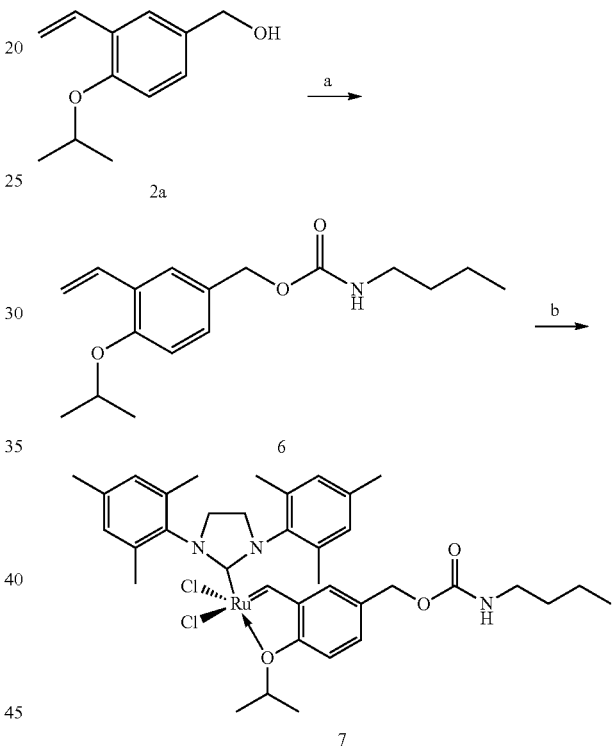

Scheme 3.

Reaction Conditions for Scheme 3:

(a) 1.05 equiv. n-butyl isocyanate, 0.01 equiv. 4-DMAP, 3 equiv. triethylamine, DCM, 45° C., 95%.

(b) 1.05 equiv. second-generation Grubbs' catalyst, 1.05 equiv. CuCl, DCM, 50° C.; column chromatography; recrystallization, 85%.

It was observed that the carbamate moiety did not notably affect the catalytic activity, and the reaction rate of 7 was comparable to the commercially available second-generation Hoveyda-Grubbs' catalyst 1b (Entries 15 and 16 in Table 1).

The recyclability of immobilized catalysts 4a-4e (Cat) in the ring-closing metathesis reaction of diene 5a to product 5b in DCM was evaluated over a time (t) of 1-2 hours (h). The results are shown in Table 2. Unless otherwise noted, all reactions were performed over 5 mol % catalyst at 0.05 M in DCM at room temperature. The percent (%) conversion was determined by gas chromatography (GC).

TABLE 2

| | Cat | Loading (mmol/g) | t | Run # | 1 | 2 | 3 | 4 | 5 | 6 | 7 | 8 | 9 | 10 |
|---|---|---|---|---|---|---|---|---|---|---|---|---|---|---|
| 1 | 4a | 0.36/0.14 | 1 h | Conv | >99 | >99 | 97 | 98 | 95 | 93 | 91 | 91 | 83 | 80 |
| 2 | 4a | 0.36/0.26 | 1 h[a] | (%) | >99 | 98 | 98 | 92 | 91 | 90 | 91 | 78 | 80 | 77 |
| 3 | 4a | 0.36/0.26 | 0.5 h[b] | | >99 | 99 | 98 | 97 | 97 | 94 | 94 | 87 | 92 | 93 |
| 4 | 4a | 0.22/0.18 | 2 h | | 99 | 99 | 97 | 96 | 94 | 97 | 85 | 82 | 79 | 79 |
| 5 | 4b | 0.44/0.16 | 2 h | | 98 | 93 | 98 | 97 | 90 | 97 | 85 | 77 | 77 | 76 |

[a]Performed at 0.1M in DCM.
[b]Performed under reflux.

Excellent conversions were observed (Table 2) for up to 6 runs (90-97%), followed by gradual loss of activity in subsequent runs. A decrease in activity to 76-80% conversions was noted for run #10 at room temperature. Without being bound by any theory, this loss in activity could be due to deactivation and/or leaching of the ruthenium carbene species, which should be in the solution phase during catalytic reactions. It was noteworthy that the recyclability was improved at an elevated temperature (Entry 3 in Table 2). Without being bound by any theory, the shorter reaction time might have reduced catalyst deactivation, and the elevated temperature might have facilitated the ethylene removal.

Ability to recycle was also examined with toluene as solvent. The results are shown in Table 3. Unless otherwise noted, all reactions were performed over 5 mol % of immobilized catalyst 4a or 4b (Cat) at 0.05 M in toluene at room temperature for a time (t) of 1-2 hours (h). The percent (%) conversion (Conv) was determined by gas chromatography (GC).

TABLE 3

| | Cat | Loading (mmol/g) | t | Run # | 1 | 2 | 3 | 4 | 5 | 6 | 7 | 8 | 9 | 10 |
|---|---|---|---|---|---|---|---|---|---|---|---|---|---|---|
| 1 | 4a | 0.36/0.14 | 1.5 h | Conv | >99 | 96 | 88 | 86 | 92 | 85 | 88 | 88 | 87 | 86 |
| 2 | 4a | 0.29/0.08 | 1.5 h | (%) | >99 | 88 | 87 | 75 | 80 | 81 | 82 | 85 | 77 | 78 |
| 3 | 4a | 0.22/0.18 | 2 h | | 99 | 89 | 80 | 85 | 85 | 81 | 86 | 75 | 79 | 77 |
| 4 | 4b | 0.44/0.16 | 2 h | | 95 | 90 | 78 | 87 | 87 | 77 | 87 | 76 | 81 | 79 |

When toluene was used as the solvent, substantial loss in activity was noted after the first recycle (Table 3). However, subsequent loss in activity was more gradual so that 77-86% conversions were achieved for run #10 at room temperature.

The performance of the MCF-supported catalysts 4, was examined for the RCM of other dienes (see Table 4). The reaction time was determined in the first run for a near-complete conversion of the specific substrate, and was kept constant for the subsequent runs to monitor any decrease in catalytic activity. Unless otherwise noted, all reactions were performed over 5 mol % of 4a at 0.05 M in DCM for 1.5 hours at room temperature. All percent (%) conversions were determined by gas chromatography (GC) except for entry 9; the percent conversions for entry 9 were determined by $^1$H-NMR spectroscopy (400 MHz).

TABLE 4

| | Substrate | Product | Run | Conversion (%) |
|---|---|---|---|---|
| 1 | 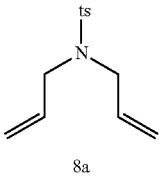<br>8a | 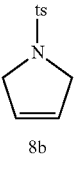<br>8b | 1<br>2<br>3<br>4<br>5<br>6<br>7<br>8 | >99 (97)[a]<br>98<br>97<br>96<br>92<br>89<br>84<br>>99[b] |
| 2 | 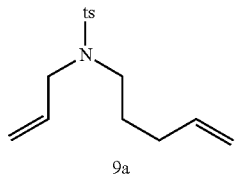<br>9a | 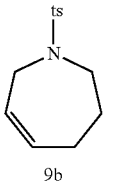<br>9b | 1<br>2<br>3<br>4<br>5<br>6<br>7 | 94 (93)[a]<br>93<br>93<br>93<br>91<br>92<br>91 |

TABLE 4-continued

| | Substrate | Product | Run | Conversion (%) |
|---|---|---|---|---|
| 3 | 10a | 10b | 1 | 94 |
| | | | 2 | 92 |
| | | | 3 | 91 |
| | | | 4 | 90 |
| | | | 5 | 88 |
| | | | 6 | 87 |
| | | | 7 | 86 |
| 4 | 11a[c] | 11b | 1 | 96 (92)[a] |
| | | | 2 | 93 |
| | | | 3 | 91 |
| | | | 4 | 85 |
| | | | 5 | 76 |
| | | | 6 | 67 |
| | | | 7 | 53 |
| 5 | 12a | 12b | 1 | >99 (97)[a] |
| | | | 2 | >99 |
| | | | 3 | 98 |
| | | | 4 | 95 |
| | | | 5 | 86 |
| | | | 6 | 86 |
| | | | 7 | 55 |
| | | | 8 | 95[c] |
| 6 | 13a | 13b | 1 | 84 |
| | | | 2 | 54 |
| | | | 3 | 23 |
| | | | 4 | 6 |
| | | | 5 | 2 |
| 7 | 14a[d] | 14b | 1 | >99 (97)[a] |
| | | | 2 | 100 |
| | | | 3 | 99 |
| | | | 4 | 98 |
| | | | 5 | 98 |
| 8 | 15a[e] | 15b | 1 | 60 (40)[f] |
| 9 | 16a | 16b | 1 | 88 |
| | | | 2 | 75 |
| | | | 3 | 71 |
| | | | 4 | 58 |
| | | | 5 | 34 |

[a]Isolated yield by column chromatography on silica gel.
[b]Performed for 6 h.
[c]Performed for 4.5 h.
[d]Performed for 1 h.
[e]Performed for 2 h.
[f]Yield for the monocyclic compound.

It was observed that RCM of the nitrogen-containing diene 8a produced the five-membered ring 8b in good yield for consecutive runs (Entry 1, Table 4), with comparable reaction rate as in the RCM of 5a. Although the recyclability was observed to drop after five runs, it was observed that the full conversion could be obtained by increasing the reaction time. Formation of the seven-membered ring containing heteroatom was also observed to be efficient, despite gradual loss in activity in seven consecutive runs (Entries 2 and 3, Table 4). Reaction of hindered diene 11a was observed to proceed more slowly, and the activity loss was observed to be more significant over consecutive runs with an increased reaction time per cycle (Entry 4, Table 4). The reaction efficiency appeared similar in the case of an internal olefin, but the recyclability was observed to be lower than in the case of the terminal olefin in Entry 1. Without being bound by any theory, it is believed that this is because the product inhibition became greater due to the increased solubility of propene evolved in DCM (Entry 5, Table 4). Catalyst 4a showed significant loss in activity over consecutive runs for RCM of substrate containing free alcohol (Entry 6, Table 4). Without being bound by any theory, this could be attributed to leaching problems, or it might be due to stronger interactions between hydroxyl groups and the reactive catalytic species.

High catalyst recyclability was demonstrated for aliphatic ether 14a (Entry 7, Table 4), which are generally known to cause more serious metal leaching due to the coordinating ability of the oxygen to ruthenium. It appeared that the catalyst system of the invention was particularly efficient for the aliphatic ether substrates, achieving 98% conversion in 1 hour for all 5 runs. The enyne 15a produced a monocyclic compound, as well as the desired bicyclic analog (Entry 8, Table 4). This lack of selectivity is consistent with other findings that the formation of the six-membered monocyclic compound was unavoidable in the catalysis by the second-generation Grubbs' catalyst. (See, for example, Michrowska, A.; Bujok, R.; Harutyunyan, S.; Sashuk, V.; Dolgonos, G.; Grela, K. *J. Am. Chem. Soc.* 2004, 126, 9318.) Macrocycle was also successfully formed over 4a, although the conversions decreased over consecutive runs (Entry 9, Table 4).

Without being bound by any particular theory, it is believed that the catalyst system is recycled by the return of the reactive catalytic species to the MCF-supported isopropoxystyrene ligand. To study the role of the reactive catalytic species over multiple runs, excess free ligand was used in a RCM of diene 5a in immobilized catalyst 4a. The results of experiments are presented in Table 5.

TABLE 5

| Ligand/Ru Loading in 4a (mmol/g) | t | Run # | 1 | 2 | 3 | 4 | 5 | 6 | 7 | 8 | 9 | 10 |
|---|---|---|---|---|---|---|---|---|---|---|---|---|
| 1 0.22/0.18 | 2 h | Conv (%) | 98 | 99 | 98 | 98 | 97 | 97 | 91 | 90 | 90 | 85 |
| 2 1.10/0.18 | 2 h | | 99 | 96 | 99 | 99 | 98 | 97 | 94 | 93 | 92 | 91 |

For both Entries 1 and 2 in Table 5, reactions were performed over 5 mol % of 4a at 0.1 M in DCM at room temperature for a time (t) of 2 hours (h). For Entry 1, 5 mol % of MCF-supported free ligands 3a (0.22 mmol ligand/g) was also added. For Entry 2, a high ligand loading and a partial Ru loading was used. The percent (%) conversion (Conv) was determined by Gas Chromatography (GC).

The catalyst was observed to recycle over 10 runs in both cases in Table 5, with better observed results in Entry 2. Although the reaction was retarded with the introduction of excess free ligands, this approach successfully improved catalyst recyclability. To compensate for the slower reaction rate, a higher concentration (0.1 M) was employed.

It was also observed that the presence of excess free ligands reduced ruthenium leaching problems over multiple cycles. In Table 6, the activity and leaching of catalyst 4a in the RCM of diene 14a was studied. Reactions for Entries 1 to 4 were performed over 5 mol % of 4a (0.36 mmol ligand/g, 0.26 mmol Ru/g) at 0.05 M in DCM. For Entries 2 and 4, ligand 3a (0.22 mmol ligand/g) was added in the specified mol %. The reaction was performed at the noted temperature (T) of either room temperature (r.t.) or reflux temperature. The time (t) was measured in hours (h). Ruthenium (Ru) residue in parts per million (ppm) was determined by inductively coupled plasma-mass spectrometry (ICP-MS), and the percent (%) conversion (Conv) was determined by gas chromatography.

TABLE 6

| Ligand | T | t | Run # | 1 | 2 | 3 |
|---|---|---|---|---|---|---|
| 1 — | r.t. | 1 h | Ru residue (ppm) [Conv. (%)] | 35 [>99] | 30 [99] | 20 [98] |
| 2 5 mol % | r.t. | 2 h | | 23 [99] | 18 [99] | 15 [98] |
| 3 — | reflux | 0.5 h | | 13 [>99] | 9 [>99] | 7 [99] |
| 4 5 mol % | reflux | 1 h | | 10 [99] | 9 [99] | 9 [99] |

Table 6 illustrates that when 5 mol % MCF-supported free ligands 3a was added to the RCM of 14a, the ruthenium concentration in the supernatant measured by ICP-MS at the end of each run was decreased, despite the longer reaction time. The suppression of ruthenium leaching was observed to be particularly significant for reaction runs at room temperature.

The results in Table 6 support the earlier observation that the ability to recycle can be enhanced by using excess free ligands and elevated reaction temperatures.

Experimental Procedure—Tables 1-6

In general, catalyst activity as a function of percent conversion in each of Tables 1 to 6 was determined by running the reactions in a vial containing a magnetic stir bar under argon at room temperature. The vial was charged with catalyst (e.g., 4a-4e in an amount of 5 μmol) and solvent (e.g., DCM). The substrate (e.g., 5a, 8a-16a in an amount of 0.1 mmol) was then injected. Conversions were monitored (e.g., by GC) after filtration through a short pad of silica gel by elution with solvent (e.g., DCM). In general, the reaction volume was 1-4 ml. For those experiments where the ability of the catalyst system to recycle was studied, these reactions were generally run in a similar manner to those for studying catalyst activity. For the recycle studies, on completion of each run, the reaction vial was centrifuged at 4000 rpm for 3 minutes, and the supernatant was characterized by flash column chromatography and GC for isolated yield and conversion, respectively. The vial was charged with another aliquot of solvent (e.g., DCM), stirred for 1 minute, and centrifuged again. One more rinse was performed before the next run was conducted with fresh substrate.

Example 1

Preparation of Ligands 3a and 3b

Step (a):

A Schlenk flask was charged with the corresponding alcohol 2a or 2b (10.0 mmol), 3-isocyanylpropyl-1-triethoxysilane (10.0 mmol), 4-dimethylpyridine (0.10 mmol), triethylamine (20.0 mmol), and dried DCM (10 ml) under argon. The reaction mixture was heated for 48 hours under reflux. DCM and triethylamine were removed under reduced pressure. Hexane (10 ml) was added, and the precipitate was removed by filtration. The filtrate was concentrated under reduced pressure, and dried under vacuum to give the corresponding carbamate as a colorless oil, which was used without further purification.

The general procedure of Step (a) using 2a (8.35 mmol) gave 3.63 g of the corresponding triethoxysilane: $^1$H-NMR (400 MHz, CDCl$_3$): δ 0.64 (t, 2H, J=8.0 Hz), 1.24 (t, 9H, J=7.2 Hz), 1.35 (d, 6H, J=6.0 Hz), 1.62 (m, 2H), 3.19 (m, 2H), 3.82 (q, 6H, J=7.2 Hz), 4.54 (septet, 1H, J=6.0 Hz), 5.03 (bs, 2H), 5.25 (dd, 1H, J=11.2, 1.4 Hz), 5.75 (dd, 1H, J=17.6, 1.4 Hz), 6.86 (d, 1H, J=8.4 Hz), 7.04 (dd, 1H, J=17.6, 11.2 Hz), 7.22 (dd, 1H, J=8.4, 2.2 Hz), 7.48 (d, 1H, J=2.2 Hz). $^{13}$C-NMR (100 MHz, CDCl$_3$): δ 7.6, 18.3, 22.1, 23.3, 43.4, 58.4, 66.4, 70.9, 106.6, 114.0, 114.3, 126.9, 128.6, 129.0, 131.7, 155.1, 156.5. MS (FAB): m/z (%) 438 (38) [M$^+$–H], 392 (20) [M$^+$-EtOH—H], 364 (16), 297 (5), 264 (18), 220 (89), 174 (100). HRMS (FAB) calculated for C$_{22}$H$_{36}$NO$_6$Si: 438.2331, found 438.2328.

The general procedure of Step (a) using 2b (4.22 mmol) gave 1.77 g of the corresponding triethoxysilane: $^1$H-NMR (400 MHz, CDCl$_3$): δ 0.68 (t, 2H, J=8.0 Hz), 1.24 (t, 9H, J=7.2 Hz), 1.33 (d, 6H, J=6.0 Hz), 1.70 (quintet, 2H, J=8.0 Hz), 3.26 (q, 2H, J=8.0 Hz), 3.83 (q, 6H, J=7.2 Hz), 4.46 (septet, 1H, J=6.0 Hz), 5.24 (dd, 1H, J=11.2, 1.4 Hz), 5.42 (bs, 2H), 5.69 (dd, 1H, J=17.6, 1.4 Hz), 6.84 (d, 1H, J=8.8 Hz), 6.96 (dd, 1H, J=8.8, 2.2 Hz), 7.02 (dd, 1H, J=17.6, 11.2 Hz), 7.22 (d, 1H, J=2.2 Hz). $^{13}$C-NMR (100 MHz, CDCl$_3$): δ 7.4, 18.7, 22.0, 22.9, 43.3, 58.3, 71.3, 114.3, 114.9, 119.0, 121.4, 128.5, 131.1, 144.4, 152.2, 154.8. MS (FAB): m/z (%) 426 (37) [M$^+$+H], 380 (100) [M$^+$-EtOH+H], 178 (69). HRMS (FAB) calculated for C$_{21}$H$_{36}$NO$_6$Si: 426.2306, found 426.2299.

Step (b):

A Schlenk flask was charged with MCF (2.05 g, 0.60 mmol TMS/g) and placed under vacuum for 24 hours at 120° C. The flask was purged with argon at room temperature, and charged with dried toluene (20 ml) and the corresponding triethoxysilane (0.85 mmol) obtained from Step (a). The resulting mixture was heated for 48 hours at 100° C. Upon cooling to room temperature, the solid was thoroughly rinsed with toluene, DCM, methanol, and DCM (50 ml each). The white solid obtained was transferred to a Schlenk flask, and dried under vacuum for 12 hours at 80° C. After cooling down to room temperature, the flask was placed in liquid nitrogen bath for 10 minutes, and HMDS (1 ml) was added under vacuum. The flask was sealed and then kept at 80° C. for 5 hours. The resulting solid was cooled to room temperature, washed thoroughly with DCM (100 ml), and then dried under vacuum for 24 hours to give the corresponding immobilized ligand as a white powder.

Following this general procedure, intermediates 3a and 3b may be obtained:

| Starting Material (amount) | Intermediate (amount) | Elemental Analysis |
|---|---|---|
| 2a (0.42 mmol) | 3a (1.00 g) Used for preparation of 4a, Entries 1 and 3-5 of Table 1) | C: 10.77 H: 1.91 N: 0.51 |
| 2a (0.85 mmol) | 3a (2.18 g) Used for preparation of 4a, Entry 2 of Table 1 | C: 8.77 H: 1.54 N: 0.40 |
| 2a (0.45 mmol) | 3a (2.00 g) Used for preparation of 4a, Entry 6 of Table 1 | C: 8.16 H: 1.66 N: 0.31 |
| 2a (2.20 mmol) | 3a (2.00 g) Used for preparation of 4a, Entries 7 and 8 of Table 1 | C: 14.15 H: 2.02 N: 1.53 |
| 2b (1.11 mmol) | 3b (1.32 g) Used for preparation of 4b, Entry 9 of Table 1 | C: 12.65 H: 1.88 N: 1.01 |
| 2b (0.60 mmol) | 3b (1.34 g) Used for preparation of 4b, Entries 10 and 11 of Table 1 | C: 9.77 H: 1.72 N: 0.62 |

Example 2

Preparation of Ligands 3c-3e

Step (a):

A two-necked flask equipped with a reflux condenser was charged with magnesium (21.0 mmol), iodine (trace), and dried THF (50 ml), and heated under reflux. 4-Bromo-2-isopropoxystyrene (20.0 mmol) in THF (50 ml) was added slowly, and the resulting mixture was stirred under reflux until magnesium disappeared. After cooling to room temperature, the turbid solution was added to a stirred solution of the corresponding dichloride (60.0 mmol) in THF (50 ml) at 0° C. The resulting solution was stirred for 18 hours at room temperature. It was concentrated under reduced pressure, and hexane (20 ml) was added slowly under stirring. The insoluble substance was filtered off, and the filtrate was concentrated and dried under vacuum for 24 hours to give the corresponding chlorosilane as an oil, which was used without further purification.

The general procedure of Step (a) using dichlorodimethylsilane (20.0 mmol) gave 5.05 g of the corresponding chlorosilane 3c: $^1$H-NMR (400 MHz, CDCl$_3$): δ 0.68 (s, 6H), 1.36 (d, 6H, J=6.0 Hz), 4.59 (septet, 1H, J=6.0 Hz), 5.27 (dd, 1H, J=11.2, 1.4 Hz), 5.78 (dd, 1H, J=17.6, 1.4 Hz), 6.91 (d, 1H, J=8.4 Hz), 7.05 (dd, 1H, J=17.6, 11.2 Hz), 7.46 (dd, 1H, J=8.4, 1.6 Hz), 7.69 (d, 1H, J=1.6 Hz). $^{13}$C-NMR (100 MHz, CDCl$_3$): δ 2.2, 22.0, 70.3, 113.0, 114.5, 126.6, 127.2, 131.7, 131.8, 133.8, 156.9.

The general procedure of Step (a) using 1,2-bis(dichlorosilyl)ethane (15.0 mmol) gave 5.01 g of the corresponding chlorosilane 3d: $^1$H-NMR (400 MHz, CDCl$_3$): δ 0.30 (s, 6H), 0.42 (s, 6H), 0.76 (s, 4H), 1.39 (d, 6H, J=6.0 Hz), 4.61 (septet, 1H, J=6.0 Hz), 5.28 (dd, 1H, J=11.2, 1.4 Hz), 5.79 (dd, 1H, J=17.6, 1.4 Hz), 6.91 (d, 1H, J=8.4 Hz), 7.10 (dd, 1H, J=17.6, 11.2 Hz), 7.37 (dd, 1H, J=8.4, 1.6 Hz), 7.61 (d, 1H, J=1.6 Hz). $^{13}$C-NMR (100 MHz, CDCl$_3$): δ −3.4, 1.0, 7.3, 11.5, 22.2, 70.3, 113.0, 114.1, 127.0, 129.1, 132.2, 132.3, 134.3, 156.1.

The general procedure of Step (a) using 1,6-bis(dichlorosilyl)hexane (20.0 mmol) gave 7.78 g of the corresponding chlorosilane 3e: $^1$H-NMR (400 MHz, CDCl$_3$): δ 0.24 (s, 6H), 0.40 (s, 6H), 0.70-0.85 (m, 4H), 1.32 (bs, 8H), 1.37 (d, 6H, J=6.0 Hz), 4.57 (septet, 1H, J=6.0 Hz), 5.24 (dd, 1H, J=11.2, 1.4 Hz), 5.76 (dd, 1H, J=17.6, 1.4 Hz), 6.88 (d, 1H, J=8.4 Hz), 7.07 (dd, 1H, J=17.6, 11.2 Hz), 7.34 (dd, 1H, J=8.4, 1.6 Hz), 7.59 (d, 1H, J=1.6 Hz). $^{13}$C-NMR (100 MHz, CDCl$_3$): δ −2.6, 1.9, 16.1, 19.2, 22.4, 23.1, 24.0, 32.8, 33.4, 70.5, 113.2, 114.1, 127.1, 130.3, 132.3, 132.5, 134.4, 156.1.

Step (b):

A Schlenk flask was charged with MCF (3.00 g, 0.80 mmol TMS/g), and placed under vacuum for 24 hours at 120° C. The flask was purged with argon at room temperature, and charged with triethylamine (0.44 ml), dried toluene (40 ml), and the corresponding chlorosilane (1.05 mmol). The resulting mixture was stirred for 24 hours at room temperature. The white solid was thoroughly rinsed by toluene, DCM, methanol, and DCM (50 ml each), which was transferred to a Schlenk flask and dried under vacuum for 12 hours at 80° C. After cooling down to room temperature, the flask was placed in liquid nitrogen bath for 10 min, and HMDS (1 ml) was added under vacuum. The flask was sealed and then kept at 80° C. for 5 hours. The resulting solid was cooled to room temperature, washed thoroughly with DCM (100 ml), and then dried under vacuum for 24 hours to give the corresponding immobilized ligand as a white powder.

Following this general procedure, intermediates 3c, 3d and 3e may be obtained:

| Amount corresponding precursor | Intermediate (amount) | Elemental Analysis |
|---|---|---|
| 1.05 mmol | 3c (3.23 g) Used for preparation of 4c, Entry 12 of Table 1 | C: 8.16 H: 1.39 N: <0.07 |
| 0.70 mmol | 3d (2.20 g) Used for preparation of 4d, Entry 13 of Table 1 | C: 9.96 H: 2.04 N: <0.06 |
| 1.05 mmol | 3e (3.46 g) Used for preparation of 4e, Entry 14 of Table 1 | C: 10.91 H: 2.07 N: <0.03 |

Example 3

Preparation of Catalysts 4a-4e

A two-necked flask equipped with a reflux condenser was charged with ligand 3a (500 mg, 0.36 mmol/g), second-generation Grubbs' catalyst (0.18 mmol), copper chloride (0.18 mmol), and dried DCM (10 ml) under argon. The reaction mixture was heated for 18 hours under reflux in stream of argon. The reaction mixture gradually changed from dark brown to deep green. After cooling to room temperature, the fine powder was washed thoroughly with DCM (100 ml) under open atmosphere, and dried under vacuum for 24 h to give the immobilized catalyst 4a (578 mg) as a green powder.

The skilled person will readily appreciate how this general procedure may be adapted to obtain catalysts 4b-4e.

Using this general procedure, catalysts 4a-4e may be obtained:

| Intermediate (amount) | Catalyst (amount) | Elemental Analysis |
|---|---|---|
| 3a (500 mg) | 4a (536 mg) Entry 1, Table 1 | |
| 3a (1.00 g) | 4a (1.04 g) Entry 2, Table 1 | |
| 3a (500 mg) | 4a (578 mg) Entries 3-5 of Table 1 | C: 15.30 H: 2.26 N: 1.07 |
| 3a (1.00 g) | 4a (1.09 g) Entry 6 of Table 1 | |
| 3a (500 mg) | 4a (546 mg) Entries 7-8 of Table 1 | C: 17.26 H: 2.31 N: 1.30 |
| 3b (250 mg) | 4b (279 mg) Entry 9 of Table 1 | |
| 3b (500 mg) | 4b (541 mg) Entries 10-11 of Table 1 | |
| 3c (500 mg) | 4c (566 mg) Entry 12 of Table 1 | C: 12.99 H: 1.97 N: 0.59 |
| 3d (2.00 g) | 4d (2.27 g) Entry 13 of Table 1 | C: 14.02 H: 2.32 N: 0.69 |
| 3e (2.00 g) | 4e (2.25 g) Entry 14 of Table 1 | C: 14.89 H: 2.43 N: 0.67 |

Although the foregoing invention has been described in some detail by way of illustration and example, and with regard to one or more embodiments, for purposes of clarity of understanding, it is readily apparent to those of ordinary skill in the art in light of the teachings of this invention that certain changes, variations and modifications may be made thereto without departing from the spirit or scope of the invention as described in the appended claims.

It must be noted that as used in the specification and the appended claims, the singular forms of "a", "an" and "the" include plural reference unless the context clearly indicates otherwise.

Unless defined otherwise all technical and scientific terms used herein have the same meaning as commonly understood to one of ordinary skill in the art to which this invention belongs.

All publications, patents and patent applications cited in this specification are incorporated herein by reference as if each individual publication, patent or patent application were specifically and individually indicated to be incorporated by reference. The citation of any publication, patent or patent application in this specification is not an admission that the publication, patent or patent application is prior art.

The invention claimed is:

1. A ring-closing metathesis catalyst composition comprising a catalyst:

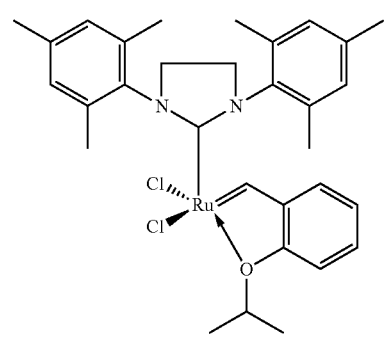

immobilized on a siliceous mesocellular foam support via a linking group, the linking group attached to the 2-position of the catalyst

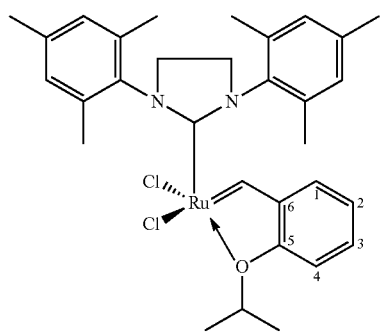

and the linking group having a formula —X—C(O)N(H)—[(C$_1$-C$_6$)alkyl]-, wherein X is (CH$_2$)$_n$O and n is from 2 to 12.

2. The catalyst composition according to claim 1, wherein the linking group is —X—C(O)N(H)CH$_2$CH$_2$CH$_2$—, and wherein X is (CH$_2$)$_n$O and n is from 2 to 12.

3. The catalyst composition according to claim 1, wherein the siliceous mesocellular foam support comprises trimethylsilyl.

4. The catalyst composition according to claim 1, wherein the siliceous mesocellular foam support comprises spherical, monodisperse siliceous mesocellular foam microparticles.

5. The catalyst composition according to claim 4, wherein the siliceous mesocellular foam support comprises pores having an average pore diameter of about 24 to about 42 nm.

6. A method for preparing a catalyst composition as defined in claim 1, the method comprising immobilizing a catalyst on a siliceous mesocellular foam support via a linking group, the catalyst having a formula

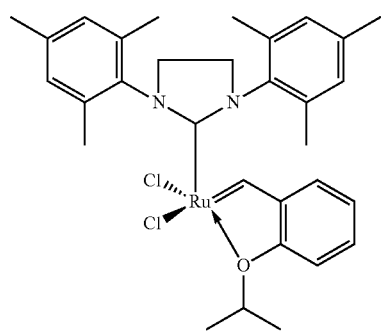

and the linking group having a formula —X—C(O)N(H)—[(C$_1$-C$_6$)alkyl]-, wherein X is (CH$_2$)$_n$O and n is from 2 to 12, the linking group attached to the 2-position of the catalyst

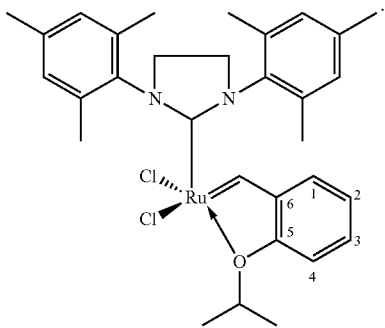

7. A method comprising catalyzing a ring-closing metathesis reaction with a catalyst composition as defined in claim 1.

8. The method of claim 7, wherein the catalyst composition is as defined in claim 2.

9. The method of claim 7, further comprising recycling the catalyst composition following completion of the ring-closing metathesis reaction.

* * * * *